United States Patent [19]

McClelland et al.

[11] Patent Number: 4,976,967

[45] Date of Patent: * Dec. 11, 1990

[54] RESIN MODULATED DRUG DELIVERY DEVICE FOR THE DELIVERY OF HMG-COA REDUCTASE INHIBITOR SALTS

[75] Inventors: Gregory A. McClelland; Gaylen M. Zentner; Stefano A. Pogany, all of Lawrence, Kans.

[73] Assignee: Merck & Co., Inc., Rahway, N.J.

[ * ] Notice: The portion of the term of this patent subsequent to Jan. 3, 2006 has been disclaimed.

[21] Appl. No.: 274,172

[22] Filed: Nov. 21, 1988

Related U.S. Application Data

[63] Continuation-in-part of Ser. No. 81,090, Aug. 13, 1987, Pat. No. 4,795,644, and a continuation-in-part of Ser. No. 91,571, Aug. 31, 1987, Pat. No. 4,814,183.

[51] Int. Cl.$^5$ .............................................. A61R 9/24
[52] U.S. Cl. ...................................... 424/473; 424/474; 424/457; 514/946
[58] Field of Search .................. 424/473, 457, 474; 514/946

[56] References Cited

U.S. PATENT DOCUMENTS 4,795,644  1/1989  Zentner ............................. 424/457
4,814,183  3/1989  Zentner ............................. 424/285

Primary Examiner—Merrell C. Cashion, Jr.
Assistant Examiner—Leon R. Horne
Attorney, Agent, or Firm—Melvin Winokur; Joseph F. DiPrima

[57] ABSTRACT

The instant invention relates to a drug-delivery device for the controlled release of HMG-CoA reductase inhibitor salts, as the therapeutically active ingredient, into an environment of use which comprises:

(A) a core composition comprising
  (1) a water insoluble, non-diffusible, charged resin entity, and
  (2) a diffusible, water soluble ionizable therapeutically active HMG-CoA reductase inhibitor salt carrying the same charge as said resin entity; and (B) an imperforate water insoluble wall surrounding said core composition and prepared from a semipermeable material substantially impermeable to core composition and permeable to the passage of an external fluid in the environment of use, with said wall having a means for release of the therapeutic agent through the water insoluble wall; or (C) a water insoluble wall surrounding said core composition and prepared from (1) a polymer material that is permeable to water but substantially impermeable to solute and (2) 0.1 to 75% by weight, based on the total weight of (1) and (2), of at least one water leachable pore forming additive dispersed throughout said wall.

17 Claims, 8 Drawing Sheets

RESIN MODULATED DRUG DELIVERY DEVICE FOR THE DELIVERY OF HMG-COA REDUCTASE INHIBITOR SALTS

This is a continuation-in-part of co-pending U.S. patent applications Ser. No. 081090, filed Aug. 3, 1987 now U.S. Pat. No. 4,795,644 and Ser. No. 091571, filed Aug. 31, 1987 now U.S. Pat. No. 4,814,183.

FIELD OF THE INVENTION

This invention pertains to both a novel and useful drug delivery device for dispensing an HMG-CoA reductase inhibitor salt to all regions of the gastrointestinal tract, regardless of the pH, at a controlled rate. The invention relates to a drug-delivery device comprising a core compartment that contains a charged, water insoluble, non-diffusible entity, herein called "charged resin", intimately mixed with a water-soluble, diffusible, ionized HMG-CoA reductase inhibitor surrounded by a substantially imperforate water insoluble semipermeable wall having a release means, herein called "hole(s)" or a porous water insoluble wall surrounding said core composition and prepared from (1) a polymer material that is permeable to water but substantially impermeable to solute and (2) 0.1 to 75% by weight, based on the total weight of (1) and (2), of at least one water leachable pore forming additive dispersed throughout said wall. In operation the soluble HMG-CoA reductase inhibitor salt and insoluble resin core components carry the same charge. The device delivers the HMG-CoA reductase inhibitor salt at a controlled rate in all regions of the gastrointestinal tract, which has a pH range generally from pH 1 to pH 8. The device thereby presents the HMG-CoA reductase inhibitor salt to a variable environment of intended use at a controlled rate.

BACKGROUND OF THE INVENTION

Hypercholesterolemia is known to be one of the prime risk factors for atherosclerosis and coronary heart disease, the leading cause of death and disability in Western countries.

There are agents known, however, that are very active antihypercholesterolemic agents which function by limiting cholesterol biosynthesis via inhibiting the enzyme, HMG-CoA reductase. These agents include the natural fermentation products, such as mevastatin, lovastatin and pravastatin, and semisynthetic analogs, such as simvastatin.

Numerous analogs and homologs of these compounds have been described in the patent literature. U.S. Patent No. 4,444,784 discloses analogs of lovastatin which possess polyhydronaphthyl moieties and various 8-acyloxy groups attached thereto. U.S. Pat. No. 4,444,784 also discloses numerous pharmaceutically acceptable salts of these analogs of lovastatin wherein the 8-acyloxy group has been elaborated broadly. The pharmaceutically acceptable salts disclosed therein include those formed from cations such as sodium, potassium, aluminum, calcium, lithium, magnesium, zinc and tetramethylammonium as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)aminomethane (hereinafter called "tromethamine"), and tetramethylammonium hydroxide.

U.S. Pat. No. 4,661,483 also discloses analogs of lovastatin wherein the 8-acyloxy group has been elaborated. Additionally, co-pending U.S. applications Ser. Nos. 859,513, now abandoned, 859,524, now abandoned 859,525, now U.S. Pat. No. 4,766,245, 8/23/88, 859,530 now abandoned 859,534, now abandoned and 859,535 now U.S. Pat. No. 4,770,871, 9/13/88 all filed on May 5, 1986, disclose further analogs of lovastatin which have functionalized 8-acyloxy groups.

Co-pending U.S. patent application, Ser. No. 092 2, 1987, discloses compounds which are analogs of lovastatin and related compounds which possess a methyl group in the 6-position in the 6β stereochemical position.

Co-pending U.S. patent application, Ser. No. 048,136, now abandoned filed May 15, 1987, discloses compounds which are analogs of lovastatin and related compounds which possess a hydroxymethyl group, acyloxymethyl group, carbamoyloxymethyl group, a carboxy group, an alkoxycarbonyl group or a carbamoyl group substituted on the 6-position of the polyhydronaphthyl moiety.

Co-pending U.S. patent application, Ser. No. 092,353, now abandoned filed Sept. 2, 1987, discloses analogs of lovastatin and related compounds which possess a hydroxyalkyl group, acyloxyalkyl or carbamoyloxyalkyl group or a ketone group substituted on the 6-position of the polyhydronaphthyl moiety.

Co-pending U.S. patent application, Ser. No. 142,377 now U.S. Pat. No. 4,857,547, 8/15/89 filed Jan. 7, 1988, discloses analogs of lovastatin and related compounds which contain two double bonds in the 4,4a- and 5,6- positons or a double bond at the 5,6- position of the polyhydronaphthyl moiety.

MEVACOR®, which contains lovastatin as the active agent, and ZOCOR®, which contains simvastatin as the active agent, are now commercially available for use as antihypercholesterolemic drugs. While these products are scientific breakthroughs and remarkably safe and effective, the reduction of the effective dosage amount which is anticipated to diminish the low incidence of adverse experiences associated which these drugs would be extremely beneficial in view of the lifetime regimen of treatment of hypercholesterolemia.

Antihypercholesterolemic agents are useful for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) which may be given in two to four divided doses. Higher doses may be favorably employed as required.

The need for systems that can deliver a drug at a controlled rate to a variable environment (e.g. gastrointestinal tract) of use over a specified period of time is well established. The use of novel, charged, water-insoluble, non-diffusable resinous powders to modulate drug release from osmotically sensitive devices with rate-controlling semipermeable walls that are permeable to water and substantially impermeable to dissolved solutes has not been disclosed in the prior art and represents an advance in drug delivery technology and device composition.

U.S. Pat. Nos. 3,854,770 and 3,916,899 disclose devices which have semipermeable walls that are permeable to water and substantially impermeable to dissolved drugs and solutes. A passageway through the semipermeable wall, disclosed as a drilled hole, is provided as an exit portal for the drug through the wall. U.S. Pat. Nos. 4,256,108; 4,160,452; 4,200,098 and 4,285,987 disclose devices which contain multiple wall layers, at least one of said walls having a drilled hole for the release of core components through a rate-controlling semipermeable membrane that is substantially impermeable to dissolved drugs and other solutes. The use of charged resins to modulate drug release from the above devices was not disclosed.

Devices for the controlled and continuous delivery of an active agent made from microporous materials are known to the prior art. Generally, the agent is embedded in or surrounded by the material and its release therefrom often is adversely influenced by external conditions. U.S. Pat. No. 3,538,214 discloses a device consisting of drug coated with a film of water-insoluble plastic containing a modifying agent that is soluble at a certain pH. When this device is in the gastro-intestinal tract, the modifying agent is partially or fully dissolved from the film by gastrointestinal fluid to form a porous film. This lets fluid through the film to dissolve the drug and leach it outwards through the pores into the tract. Controlled release is difficult to achieve with this device because the selection of the modifying agent is based on the unknown acid and alkaline state of the gastro-intestinal tract which concomitantly influences pore formation and the exposure of drug to fluid. A similar device is disclosed in U.S. Pat. No. 2,928,770. The device of this patent consists of an outer layer of drug coated onto a porous material having its pores filled with a softened wax that is supposedly removed in the gastrointestinal tract by the alimentary fluid. This device cannot be relied on for controlled release because it too requires in situ pore formation which is dominated by unregulated external conditions and not by the device. The use of pore formers in substantially water impermeable polymers is disclosed in J. Pharm. Sci. 72, p. 772–775 and U.S. Pat. Nos. 4,244,941; 4,217,898; and 3,993,072. These devices release the core components by simple diffusion. U.S. Pat. No. 3,957,523 discloses a device which has a pH sensitive pore former in the device wall. U.S. Pat. Nos. 4,309,996; 4,320,759; 4,235,236 disclose layered devices with a microporous coat containing a drug layer and a swelling polymer layer acting as the driving force for delivery of agents. The use of charged resins to modulate drug release from the above devices was not disclosed.

U.S. Pat. No. 4,221,778 discloses ion-exchange resin drug complexes as delivery devices where the resin and drug carry opposite charges and osmotic factors are not included; drug release is actuated by exchange of the drug with another ion which dislodges the drug from the resin.

DETAILED DESCRIPTION OF THE DRAWINGS

Figure 1:
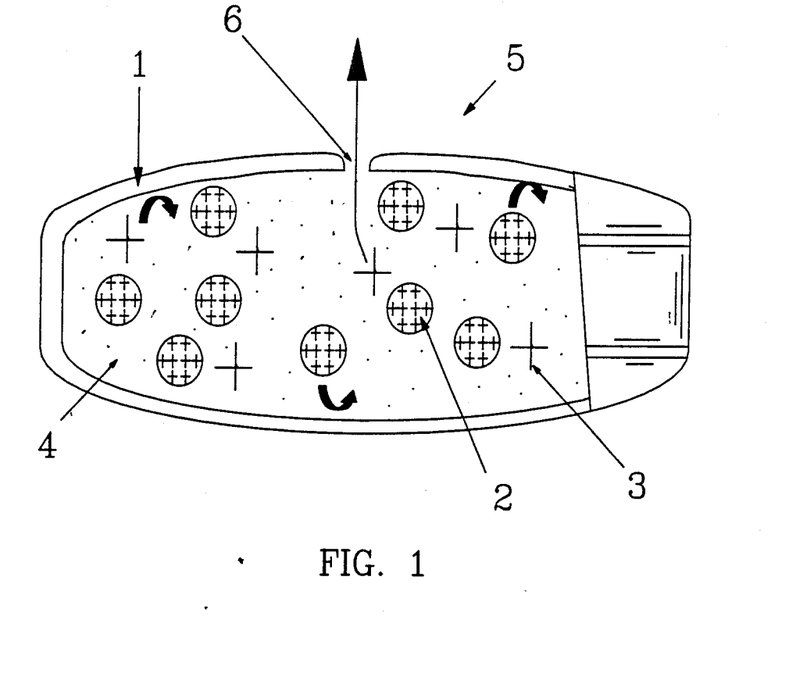
FIG. 1 is a schematic representation of one embodiment of the instant invention wherein the rate controlling wall is an imperforate semipermeable wall with a release means.
Figure 2:
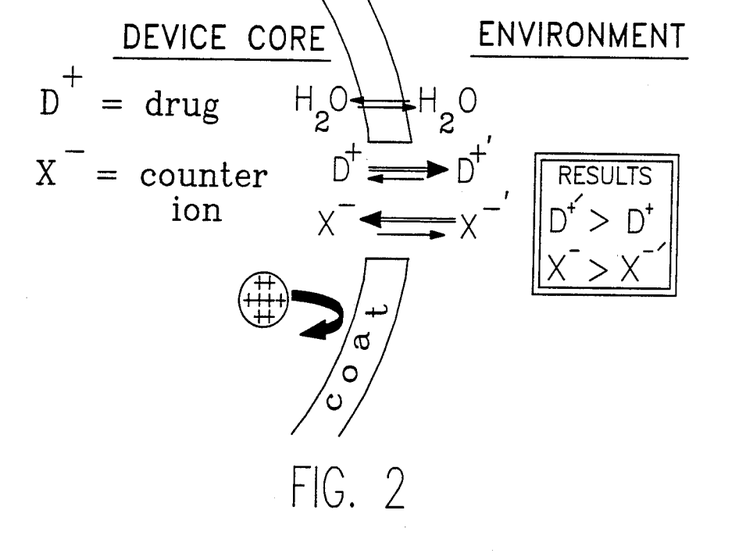
FIGS. 2 and 4 illustrate in addition to osmotic flow, the movement of the drug will be subject to Donnan effects which will modulate the release behavior of the drug from the devices.

FIG. 1 is a schematic representation of one embodiment of the instant invention wherein the rate controlling wall is imperforate. The device, 5, has a core composition comprised of drug species, 3, charged resin(s), 2, and other excipients, 4, as needed to form a tablet suitable for the application of a semipermeable, rate-determining, water-insoluble wall, 1, which contains a mechanically or optically produced hole(s), 6, for exit of the drug species from the core. As indicated by the bold arrows, in operation the insoluble resin, 2, will not permeate the wall, 1, or hole, 6, whereas the dissolved drug species, 3, and excipients, 4, are freely released through the hole in response to osmotic and concentration gradients. In the intended environments of use, typically aqueous environments, the drug, 3, and resin, 2, carry the same electrostatic charge. In addition to osmotic flow, the movement of the drug, 3, will be subject to Donnan effects which will modulate the release behavior of the drug from the device in a fashion similar to that illustrated in FIG. 2. Conditions of electrical neutrality dictate an unequal distribution of permeable charged species across any barrier that is selectively impermeable to the charged resin. This phenomena favors the movement of drug bearing a like charge away from the resin, resulting in a modulation of the drug release profile associated with the mass transport effectuating concentration and osmotic gradients.

Figure 1A:
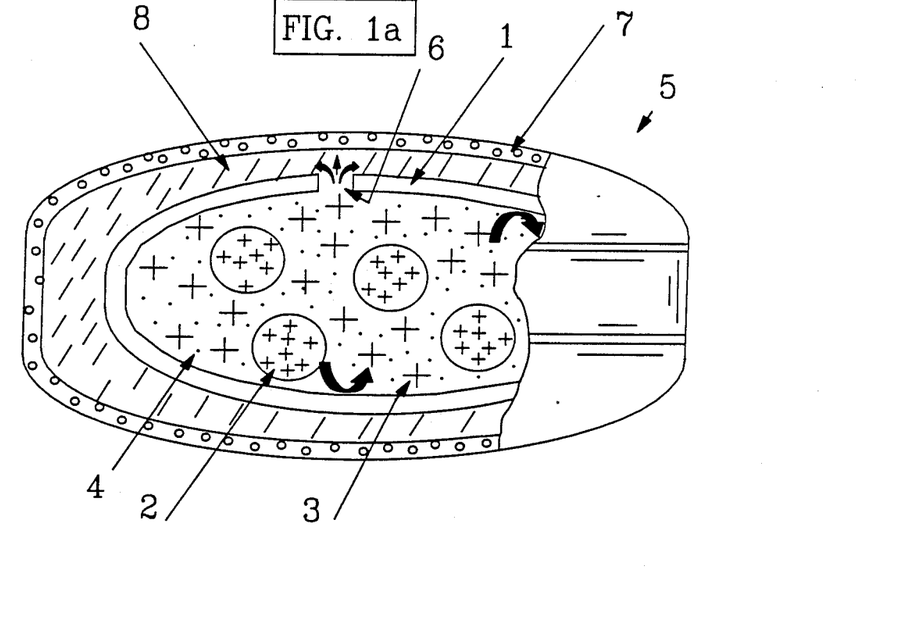
FIG. 1a is another embodiment of the instant invention with an imperforate semipermeable wall.

FIG. 1a is another embodiment of the instant invention where the imperforate semipermeable wall, 1, is coated with a layer of material, 8, that is soluble in fluids of the intended environment of use (commonly aqueous), with a microporous wall, 7, separating the layer, 8, from the external environment. The compound(s) of layer, 8, dissolve and then freely permeate the microporous wall, 7, in a fluid environment, creating a fluid filled zone separating the microporous and semipermeable walls. Drug laden solution that is pumped through the hole, 6, at a rate controlled by the semipermeable wall, 1, enters the now fluid layer, 8, where it may then freely permeate microporous wall, 7, to the exterior. All other components were defined previously.

Figure 1B:
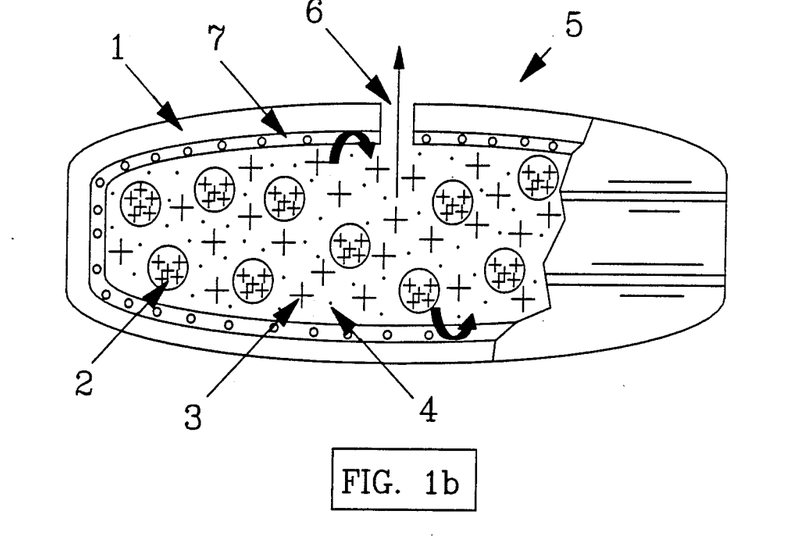
FIG. 1b is another embodiment of the instant invention with an imperforate semipermeable wall.

FIG. 1b is another embodiment of the instant invention with an imperforate semipermeable wall. As configured, the drug containing core is coated with a laminate structure comprised of a microporous wall, 7, immediately contacting the core, and an overcoating semipermeable wall, 1. The microporous wall serves as a base coating to lend mechanical strength and support to the rate controlling semipermeable wall. A hole, 6, is provided as an exit portal for the drug solution. Other components were defined previously.

Figure 4:
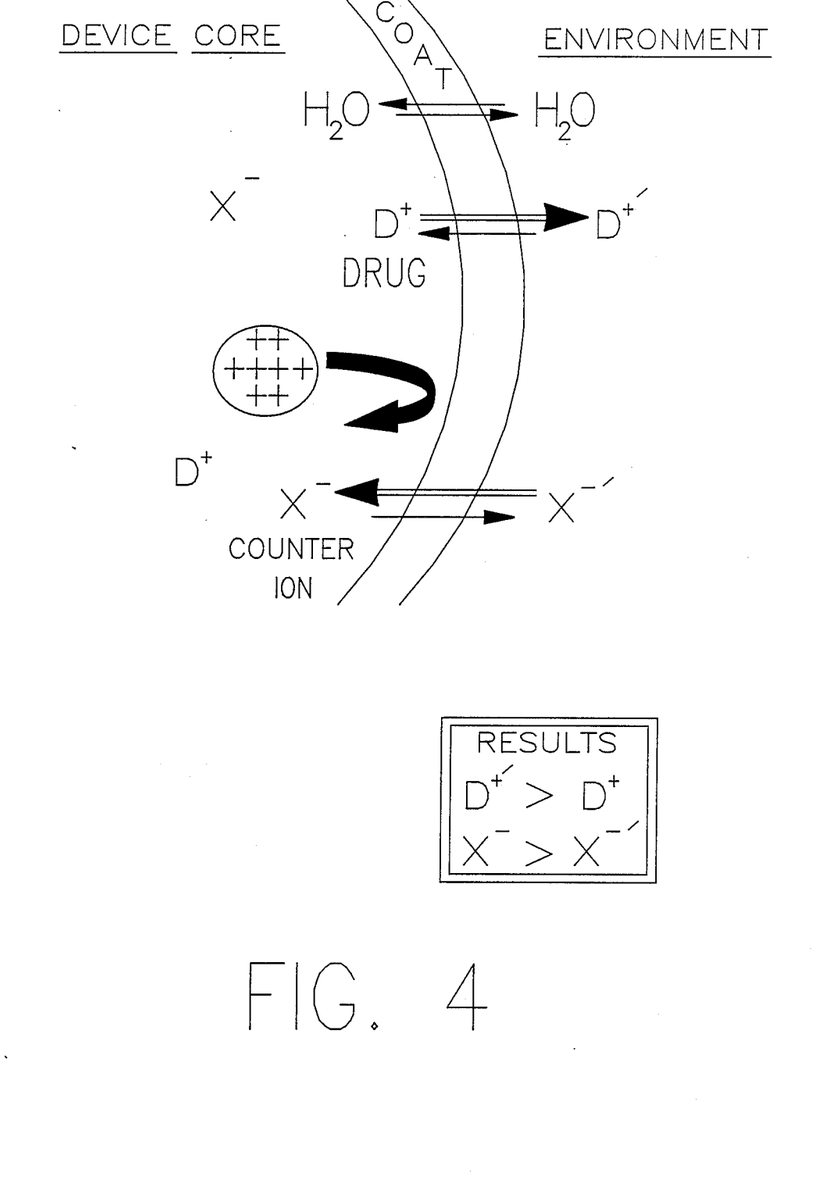
Figure 5:
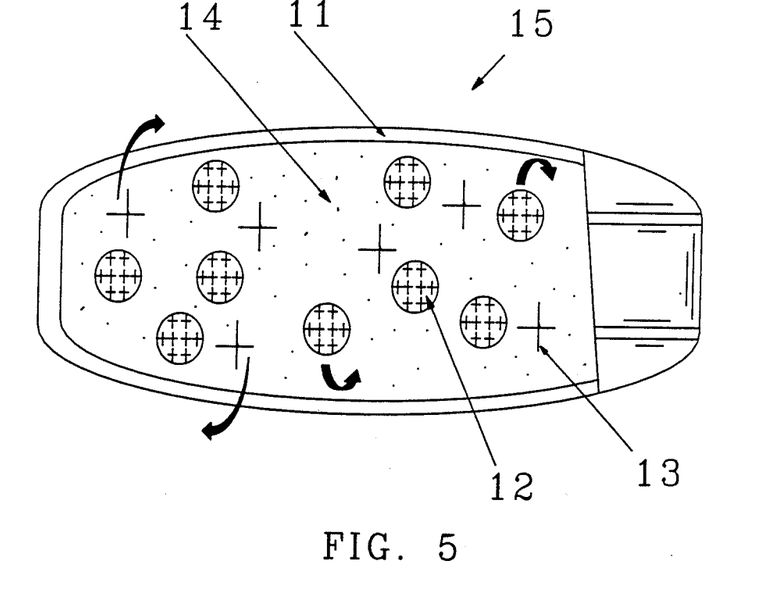
FIG. 5 is a schematic representation of the instant invention with a microporous rate-controlling wall.

FIG. 5 is a schematic representation of the instant invention with a microporous rate-controlling wall. The device, 15, has a core composition comprised of drug species, 13, charged resin(s), 12, and other excipients, 14, as needed to form a tablet suitable for the application of a microporous, rate-determining, water-insoluble wall, 11. As indicated by the bold arrows, in operation the insoluble resin, 12, will not permeate the wall, 11, whereas the dissolved drug species, 13, and excipients, 14, are freely permeable in response to osmotic and concentration gradients. In the intended environments of use, typically aqueous environments, the drug, 13, and resin, 12, carry the same electrostatic charge. These conditions impose Donnan-like effects onto the release behavior of the drug from the device as illustrated in FIG. 4. Conditions of electrical neutrality dictate an unequal distribution of permeable charged species across a coat that is impermeable to a charged resin. This phenomena favors the movement of drug bearing a like charge away from the resin, resulting in a modulation of the drug release normally associated with the mass transport effectuating concentration and osmotic gradients.

OBJECT OF THE INVENTION

It is an immediate object of this invention to disclose a novel device for delivering drug to produce a beneficial effect. Charged, insoluble, resins bearing an electrostatic charge identical to that of a drug are disclosed for modulation of drug release from a device coated with a semipermeable wall that is breeched by an introduced hole(s) or coated with a microporous wall.

Another object of the invention is to provide a device for delivering drugs to all parts the gastrointestinal tract at a substantially constant rate, regardless of the pH of the gastrointestinal tract, through a complex synergistic mechanism that incorporates aspects of diffusion, osmosis, and Donnan-like electrostatics.

Another object of the invention is to provide a drug delivery system that is readily manufacturable to deliver a pre-determined dose of a drug(s) at a programmed rate from compositions of matter in the varied geometries and sizes of tablets, beads, pellets, multi-particulates, and such related dosage forms as familiar to those skilled in the art for oral, buccal, vaginal, rectal, nasal, ocular, aural, parenteral and related routes of administration.

Another object of the invention is to provide a drug delivery device for delivering drugs over a range of release rates as controlled by the device, and which device maintains its physical and chemical integrity throughout the release period.

Other objects, features and advantages of the invention will be apparent to those skilled in the art from the following detailed description of the invention taken in conjunction with the drawings and accompanying claims.

BRIEF DESCRIPTION OF THE INVENTION

A device is disclosed for the controlled delivery of HMG-CoA reductase inhibitor salts, as the beneficial agent. The agent is delivered to the environment surrounding the device at a substantially constant rate for a specified period with a reduced dependence on the environmental pH. The device is comprised of a core compartment containing, (1) a charged, water insoluble, non-diffusible component, and, (2) at least one diffusable water soluble ionizable HMG-CoA reductase inhibitor salt. The core is surrounded by a water insoluble wall formed of a semipermeable material substantially impermeable to core components and permeable to the passage of an external fluid in the environment of use, with said wall having a means for release of the HMG-CoA reductase inhibitor salt through the water insoluble wall or the core is surrounded by a water insoluble wall containing leechable pore forming additive(s) dispersed thoughout said wall, with said wall being impermeable to the charged resin and permeable to the drug.

In operation the charged resins (often polymeric resins) and the water soluble ionizable HMG-CoA reductase inhibitor have the same electrostatic charge and do not form an ion exchange complex. Rather, a Donnan influenced mass transport phenomena of the beneficial agent is effected through the release means in the device, actuated by water from the environment, with migration of the freely mobile species (beneficial agent) away from the non-mobile species (charged resin). Thus, the device releases the beneficial agent through the release means of the wall at a controlled rate with reduced pH dependency.

DETAILED DESCRIPTION OF THE INVENTION

The instant invention is directed to an osmotic pump for the controlled release of HMG-CoA reductase inhibitor salts to an environment of use, said pump comprising:
(A) a core composition comprising
 (1) a water insoluble, non-diffusible charged resin entity, and
 (2) a therapeutically effective amount of a diffusible, water soluble, ionizable HMG-CoA reductase inhibitor salt carrying the same charge as said resin entity surrounded by
(B) a rate controlling water insoluble wall, prepared from:
 (1) a polymer permeable to water but substantially impermeable to solute and
 (2) 0.1 to 75% by weight, based on the total weight of (1) and (2), of at least one pH insensitive water leachable pore forming additive dispersed throughout said wall; or
(C) an imperforate water insoluble wall surrounding said core composition, prepared from a semipermeable material substantially impermeable to the core composition and permeable to the passage of an external fluid in the environment of use, with said wall having a hole(s) for release of the therapeutic agent through the water insoluble wall.

Other microporous walls and soluble layers that are freely permeable to dissolved solutes may be incorporated in conjunction with the imperforate semipermeable wall.

The specific salts of HMG-CoA reductase inhibitors of this invention are the tromethamine salt of the known compounds which are represented by the following general structural formula (I):

wherein:
R$^1$ is selected from:

(1) $C_{1-10}$ alkyl;
(2) substituted $C_{1-10}$ alkyl in which one or more substituent(s) is selected from
   (a) hydroxy,
   (b) $C_{1-5}$ alkoxycarbonyl,
   (c) $C_{1-5}$ acyloxy,
   (d) $C_{3-8}$ cycloalkyl, and
   (e) phenyl and;
(3) $C_{3-8}$ cycloalkyl; p0 $R^2$ is selected from:
(1) methyl;
(2) substituted $C_{1-10}$ alkyl in which the substituent is selected from:
   (a) hydroxy, or
   (b) $C_{1-5}$ acyloxy, and
(3) $C_{1-5}$ alkoxycarbonyl and;
(4) hydroxy; and
a, b, c and d each represent single bonds or one of a, b, c and d represents a double bond or both a and c or both b and d represent double bonds, provided that when a is a double bond, $R^2$ is methyl, substituted $C_{1-10}$ alkyl or $C_{1-5}$ alkoxycarbonyl.

One further embodiment of this invention is the class of osmotic delivery devices which contain a compound of the formula (I) wherein:
$R^2$ is selected from:
(1) methyl; or
(2) hydroxy.

One subclass of this embodiment are the osmotic delivery devices which contain the compounds of the formula (I) wherein:
$R^1$ is $C_{1-10}$ alkyl.

Illustrative of this subclass are those devices containing the compounds of the formula (I) wherein $R^1$ is 1-methylpropyl or 2,2-dimethylpropyl.

Except where specifically defined to the contrary, the terms "alkyl", "alkoxy" and "acyl" include both the straight-chain and branched-chain species of the term. Further, where appropriate, the compounds in this application may possess a substituent in the 6-position in either the 6α or 6β stereochemical position.

Exemplifying this subclass are those devices containing the compounds of the formula (I) wherein both a and c represent double bonds, especially the compounds:
 (1) 7-[1,2,6,7,8,8a(R)-hexahydro-2(S),6(R)dimethyl-8(S)-(2,2-dimethylbutyryloxy)-naphthalenyl-1(S)]-3(R),5(R)-dihydroxyheptanoate tris(hydroxymethyl)methylammonium salt;
 (2) 7-[1,2,6,7,8,8a(R)-hexahydro-2(S),6(R)-dimethyl-8(S)-(2(S)-methylbutyryloxy)-naphthalenyl-1(S)]-3(R),5(R)-dihydroxyheptanoate tris(hydroxymethyl)methylammonium salt;
 (3) 7-[1,2,6,7,8,8a(R)-hexahydro-2(S) methyl 6(S)-hydroxy 8(S)-(2(S)-methylbutyryloxy)-naphthalenyl-1(S)]-b 3(R),5(R)-dihydroxyheptanoate tris(hydroxymethyl)methylammonium salt; and
 (4) 7-[1,2,6,7,8,8a(R)-hexahydro-2(S)-methyl 6(R)-hydroxy-8(S)-(2(S)-methylbutyryloxy-naphthalenyl-1(S)]-3(R),5(R)-dihydroxyheptanoate tris(hydroxymethyl)methylammonium salt.

Also exemplifying this subclass are those devices containing the compounds of the formula (I) wherein each of a, b, c and d represents single bonds, especially 7-[1,2,3,4,4a(S),5,6,7,8,8a(S)-decahydro-2(S),6(R)-dimethyl-8(S)-(2,2-dimethylbutyryloxy)-naphthalenyl-1(S)]-3(R),5(R)-dihydroxyheptanoate tris(hydroxymethyl)methylammonium salt.

The expression water insoluble, non-diffusible, charged resin entity as used herein broadly includes any electrostatically charged or electrostatically chargeable species incapable of penetrating through the device wall. Representatives include: (a) anionic resins with acrylic, methacrylic or phenolic polymeric backbones with phosphonic acid or carboxylic acid active groups such as Dowex CCR-1, Amberlite IRC-50, Amberlite IRP-64, Zeo Karb 226, and the like; (b) anionic resins with polystyrene or phenolic polymeric backbones with varying degrees of cross-linkage containing an active group of sulfonic acid such as Amberlite 200, Dowex 50, Duolite C- 3, and the like. An extensive but not limiting list of charged resins can be found in the *Encyclopedia of Polymer Science and Technology*, Volume 7, pp. 692–742, Interscience Pub, Wiley and Sons, 1967.

Another group of charged resins that could be employed have derivatized cellulose as the principal support medium. An extensive but not limiting list of negatively charged cellulosics can be found in *The Tools of Biochemistry*, Terrance G. Cooper, p. 143, Wiley and Sons, Inc., 1977. Other negatively charged entities include charged silicates, charged clays, charged earths and zeolites.

The core compartment containing the water soluble HMG-CoA reductase inhibitor salt and water insoluble charged resin, as described herein, is typically in the form of a solid conventional tablet, pellet or particulate. The core can be comprised of a mixture of agents combined to give the desired manufacturing and delivery characteristics. The number of agents that may be combined to make the core is substantially without an upper limit with the lower limit equalling two components. It may be useful to buffer the core compartment to keep the electrostatic charge of the drug the same as that of the charged resin.

The preferred specifications for the core are summarized below and include:
1. Core Drug Loading (size)—0.05 nanograms to 2 grams or more (includes dosage forms for humans).
2. Osmotic pressure developed by a solution of the core—8 to 500 atmospheres, typically, with commonly encountered water soluble drugs and excipients; however osmotic pressures greater than zero are within guidelines.
3. Core solubility—continuous, uniform release (zero-order kinetics) of 90% or greater of the initially loaded core mass is theoretically predicted if the ratio of the dissolvable core mass solubility, S, to the dissolvable core mass density, $\rho$, that is $S/\rho$, is 0.1 or lower. Typically this occurs when 10% of the initially loaded dissolvable core mass saturates a volume of external fluid equal to the total volume of the initial dissolvable core mass.

$S/\rho$ ratios greater than 0.1 fall within the workings of the invention and result in lower percentages of initial core mass delivered under zero-order kinetics. $S/\rho$ can be selected to give acceptable combined characteristics of stability, release rate, and manufacturability.
4. Water insoluble charged resin component—0.01 to 75% by weight of the total core mass with a charge capacity of 0.01 to 50 mEq/g, preferably 0.01 to 15 mEq/g.

In cases where the drug has the desired solubility, osmotic pressure, density, stability, and manufacturability characteristics, there is no critical upper limit as to the amount that can be incorporated into a core mass and typically will follow the core loading (size) specification 1. The lower limit ratio of drug to excipient is dictated by the desired osmotic activity of the core composition, the desired time span and profile of release, and the pharmacological activity of the drug. Generally the core will contain 0.01% to 90% by weight or higher, of an active agent in mixture with another solute(s). Representative of compositions of matter that can be released from the device and can function as a solute are, without limitation, those compositions soluble in fluids inside the core compartment as described.

The HMG-CoA reductase inhibitor salt can be in the core compartment as a solution, dispersion, paste, cream, particle, granule, emulsion, suspension or powder. Also, the drug can be mixed with a binder, dispersant, emulsifier or wetting agent and dyes.

The amount of drug, or drug admixed with other osmotically active solutes and buffers present in the device, is generally initially in excess of the amount that can be dissolved in the fluid that enters the reservoir. Under this physical state when the drug is in excess and combined with charged resin, the device will osmotically operate with Donnan-like modulation to give a substantially constant rate of release. The drug release pattern can also be varied by having different amounts of drug in the reservoir to form solutions containing different concentrations of agent for delivery from the device. Generally, the device can house from 0.05 mg to 2 grams drug or more, with individual devices containing, for example, 5 mg, 25 mg, 50 mg, 100 mg and the like.

Mixtures of drug with other pH modifying and/or osmotically active compounds may be used to attract fluid into the device producing a solution of compound which is delivered from the device, concomitantly transporting drug to the exterior of the device. Examples include but are not limited to magnesium sulfate, magnesium chloride, sodium chloride, lithium chloride, potassium sulfate, sodium carbonate, potassium carbonate, potassium bicarbonate, sodium sulfite, lithium sulfate, potassium chloride, calcium bicarbonate, sodium sulfate, sodium bicarbonate, sodium bitartrate, citric acid, adipic acid, potassium or sodium mono- or diphosphate, calcium lactate, d-mannitol, urea, inositol, sorbitol, pentaerythritol, magnesium succinate, magnesium oxide, magnesium hydroxide, tromethamine, tartaric acid, carbohydrates such as raffinose, sucrose, glucose, $\alpha$-d-lactose monohydrate, mixtures thereof, and the like. The compound may be present in excess and it can be in any physical form such as particle, crystal, pellet, tablet, strip, film or granule.

One type of rate controlling wall of the invention is a material that is semi-permeable, can form imperforate films, and does not adversely affect the drug, animal body, or host, for example, a material that is permeable to an external fluid such as water and the like while essentially impermeable to a selected product, drugs, agents, resins or to other compounds in the device. The wall may be applied by spray coating procedures. The selectively-permeable material or membrane forming the wall is insoluble in body fluids and non-erodible or it can be bioerodible after a predetermined period with bioerosion corresponding to the end of the active drug release period. In each instance it is permeable to solvent but not to solute and resin and is suitable for construction of the osmotic powered device. Typical materials for forming the wall include membranes known to the art as osmosis and reverse osmosis membranes. Generally, membranes having a fluid permeability of 0.01 to 10 cc/cm$^2$/hour or day or higher at atmospheric pressure against a saturated product solution or saturated solute solution at the temperature of use while simultaneously possessing a high degree of impermeability to the product or solute are useful for manufacturing the devices of the invention. Of course, other semipermeable membranes operable for the purposes of the invention can also be used within the spirit of the invention.

Additional, preferred specifications for the imperforate semipermeable wall include:

1. Plasticizers and Flux Regulating Additives: 0 to 50, preferably 0.001 to 50, parts per 100 parts wall material.
2. Surfactant Additives: 0 to 40, preferably 0.001 to 40, parts per 100 parts wall material.
3. Wall Thickness: 1 to 1,000, preferably 20 to 500, microns typically, although thinner and thicker fall within the invention.

A second type of rate controlling wall of the invention is a water insoluble, permeable, rate controlling microporous wall as described herein, which may be applied to core composition masses by spray coating procedures. The wall is comprised of (a) polymeric material that is insoluble in the fluids of the environment of intended use (usually water), (b) other added excipients that will dissolve in the environmental fluids or leach out of the wall. The leached wall is a sponge-like structure composed of numerous open and closed cells that form a discontinuous interwoven network of void spaces when viewed with a scanning electron microscope. This controlled porosity wall serves as both the water entry and core composition solution exit sites. The wall is impermeable to the charged resin and permeable to both water and solutes, and as constituted in the environment of use has a small solute reflection coefficient, $\sigma$, and displays poor semipermeable characteristics when placed in a standard osmosis cell.

The specifications for the microporous wall are summarized below and include:

1. Fluid Permeability of the wall: $6.96 \times 10^{-18}$ to $6.96 \times 10^{-14}$ cm$^3$ sec/g (equivalent to $10^{-5}$ to $10^{-1}$ cm$^3$ mil/cm$^2$ hr atm).
2. Reflection Coefficient: Microporous coats to have a reflection coefficient, $\sigma$, defined as:

$$\sigma = \frac{\text{osmotic volume flux} \times \text{hydrostatic pressure difference}}{\text{osmotic pressure difference} \times \text{hydrostatic volume flux}}$$

where $\sigma$ is less than 1, usually less than 0.8, preferrably less than 0.5 and most preferrably less than 0.1.

Additional, preferred specifications for the microporous wall include:

1. Plasticizers and Flux Regulating Additives: 0 to 50, preferably 0.001 to 50, parts per 100 parts wall material.
2. Surfactant Additives: 0 to 40, preferably 0.001 to 40, parts per 100 parts wall material.
3. Wall Thickness: 1 to 1,000, preferably 20 to 500, microns typically although thinner and thicker fall within the invention.
4. Microporous Nature: 5% to 95% pores between 10 angstroms and 100 microns diameter.
5. Pore Forming Additives: 0.1 to 75%, preferably 0.1 to 50%, by weight, based on the total weight of pore forming additive and polymer, pore forming additive, preferably: (a) 0.1 to 50%, preferably 0.1 to 40%, by weight solid additive; (b) 0.1 to 40% by weight liquid additive, but no more than 75% total pore formers.

Any polymer permeable to water but impermeable to solutes as previously defined may be used. Examples include cellulose esters such as cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose triacylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate, methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate, beta glucan acetate, beta glucan tri-acetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethylcellulose, cellulose, hydroxylated ethyleneyinylacetate, poly(ortho ester)s, polyacetals, semipermeable polyglycolic or polylactic acid and derivatives thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, polyacrylate and polymethacrylate polymers, and derivatives and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

The expression "release means" or hole(s) as used herein are comprised of those means and methods suitable for osmotically releasing the drug from the core through the semipermeable wall. The expression includes the following: an aperture, orifice, bore, porous element through which product can migrate, hollow cellulose acetate fibers suitable for passing the drug, capillary tubes, cracks, and the like. The expression also includes bioerodible materials that erode in the environment of use to produce an osmotic passageway of pre-controlled dimensions. Typical bioerodible materials suitable for forming a passageway include erodible poly(glycolic) acid and poly(lactic) acid fibers, poly(ortho esters), erodible gelatinous filaments, poly(vinyl alcohol), and the like.

Water insoluble, permeable, non-rate controlling microporous walls may be applied to core composition masses prior to the application of the imperforate semipermeable wall or subsequent thereto by spray coating procedures. The microporous wall may either directly contact the imperforate semipermeable wall to form a bilaminate structure, or, the microporous wall may be separated from the imperforate semipermeable wall by a layer of fluid soluble material, which may optionally contain drug, which dissolves in the environment of use, creating a fluid layer separating the microporous and semipermeable walls. This microporous wall is comprised of (a) polymeric material that is insoluble in the fluids of the environment of intended use (usually water), (b) other added excipients that will dissolve in the environmental fluids or leach out of the wall. The leached wall is a sponge-like structure composed of numerous open and closed cells that form a discontinuous interwoven network of void spaces when viewed with a scanning electron microscope. The wall is permeable to both water and solutes, and as constituted in the environment of use has a small solute reflection coefficient, and displays poor semipermeable characteristics when placed in a standard osmosis cell. Additional specifications for this microporous wall include:

1. Wall Thickness: 1 to 1,000, preferably 20 to 500, microns typically although thinner and thicker fall within the invention.

2. Pore Forming Additives: 0.1 to 75%, by weight, based on the total weight of pore forming additive and polymer, pore forming additive, preferably: (a) 0.1 to 50% by weight solid additive; (b) 0.1 to 40% by weight liquid additive.

A controlled porosity wall can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is ascertained by measuring the observed pore diameter at the surface of the material under the electron microscope. Generally, materials possessing from 5% to 95% pores and having a pore size of from 10 angstroms to 100 microns can be used.

Pore forming additives may be used in the instant invention. The microporous wall may be formed in situ, by a pore-former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like; the alkaline earth metal salts such as calcium chloride, calcium nitrate, and the like; the transition metal salts such as ferric chloride, ferrous sulfate, zinc sulfate, cupric chloride, and the like. Water may be used as the pore-former. The pore-formers include organic compounds such as dimethyl sulfone, nicotinamide, and saccharides. The saccharides include the sugars sucrose, glucose, fructose, mannose, galactose, aldohexose, altrose, talose, lactose, monosaccharides, disaccharides, and water soluble polysaccharides. Also, sorbitol, pentaerythritol, mannitol, organic aliphatic and aromatic ols, including diols and polyols, as exemplified by polyhydric alcohols, poly(alkylene glycols), polyglycols, alkylene glycols, poly($\alpha,\omega$)alkyl enediols esters or alkylene glycols, polyvinylalcohol, polyvinylpyrrolidone, and water soluble polymeric materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of water soluble inorganic and organic compounds and salts, carbohydrates, polyols, polyalkylene glycols, poly($\alpha,\omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes: A Structural Perspective,* 2nd Ed., by R. E. Kesting, Chapters 7 and 8, 1985, published by John Wiley & Sons, Inc.; *Chemical Reviews*, Ultrafiltration, Vol. 18, pages 373 to 455, 1934; *Polymer Eng. and Sci.*, Vol. 11, No. 4, pages 284 to 288, 1971, *J. Appl. Poly. Sci.*, Vol. 15, pages 811 to 829, 1971, and in U.S. Pat. Nos. 3,565,259; 3,615,024; 3,751,536; 3,801,692; 3,852,224; and 3,849,528.

It is generally desirable from a preparation standpoint to mix the polymers which will comprise either the semipermeable or microporous walls in a solvent. Exemplary solvents suitable for manufacturing the wall of the instant device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n butyl acetate, methyl isobutyl ketone, methyl ethyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone-methanol (80:20), acetone-ethanol (90:10), methylene dichloride-ethanol (80:20), ethyl acetate-ethanol (80:20), ethylene dichloride-methanol (80:20), methylene dichloride-methanol (50:50), methylene dichloride-methanol (78:22), acetone-water (90:10), chloroform-ethanol (80:20), methylene dichloride-ethanol (79:21), methylene chloride-methanol-water (15:10:1), carbon-tetrachloride-methanol (70:30), expressed as (weight:weight), and the like. Water based latex forms of suitable polymers are also within the guidelines of the invention.

Exemplary plasticizers suitable for the present wall forming purposes include plasticizers that lower the temperature of the second-order phase transition of the wall or the elastic modulus thereof, and also increase the workability of the wall and its flexibility. Plasticizers may increase or decrease the permeability of the wall to fluids including water and aqueous solutions. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, polyethylene glycols, polypropylene glycols, and halogenated phenyls. Generally, from 0.001 to 50 parts of a plasticizer or a mixture of plasticizers are incorporated into 100 parts of wall forming material.

Exemplary plasticizers include dialkyl phthalates, dicycloalkyl phthalates, diaryl phthalates and mixed alkylaryl as represented by dimethyl phthalate, dipropyl phthalate, dioctyl phthalate, di-(2-ethyl-hexyl)-phthalate, di-isopropyl phthalate, diamyl phthalate and dicapryl phthalate; alkyl and aryl phosphates such as triethyl phosphate, tributyl phosphate, trioctyl phosphate, tricresyl phosphate and triphenyl phosphate;

alkyl citrate and citrate esters such as tributyl citrate, triethyl citrate, and acetyl triethyl citrate; alkyl adipates such as dioctyl adipate, diethyl adipate and di-(2-methyoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol dibutyrate and triethylene glycol dipropionate. Other plasticizers include polyethylene glycol 400, polyethylene glycol 20,000, camphor, N-ethyl-(o- and p-toluene) sulfonamide, chlorinated biphenyl, benzophenone, N-cyclohexyl-p-toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibit permanence as seen by their tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter $\chi$, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the other wall forming materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability (flux) through the wall. The agent can be preselected to increase or decrease the fluid flux. Agents that produce a marked increase in permeability to a fluid such as water, are often essentially hydrophilic, while those that produce a marked decrease in permeability to fluids such as water, are often essentially hydrophobic. The flux regulators in some embodiments also can increase the flexibility and porosity of the lamina. Examples of flux regulators include polyhydric alcohols and derivatives thereof, such as polyalkylene glycols of the formula H—(O—alkylene)$_n$—OH wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula H—(OCH$_2$CH$_2$)$_n$—OH wherein n is typically 5 to 5.7, 8.2 to 9.1, 12.5 to 13.9, 29 to 36, 29.8 to 37, 68 to 84, and 158 to 204, respectively. Other polyglycols include the low molecular weight glycols of polypropylene, polybutylene and polyamylene.

Additional flux regulators include poly ($\alpha,\omega$) alkylenediols wherein the alkylene is straight or branched chain of from 2 to 10 carbon atoms such as poly(1,3)-propanediol, poly(1,4) butanediol, poly(1,5)pentanediol and poly(1,6)hexanediol. The diols also include aliphatic diols of the formula HOC$_n$H$_{2n}$OH wherein n is from 2 to 10 and diols are optionally bonded to a non terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO—(alkylene—O)$_n$—H wherein the divalent alkylene radical includes the straight chain groups and the isomeric forms thereof having from 2 to 6 carbons and n is 1 to 14. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present wall forming purpose are those surfactants, when added to a wall forming material and other materials, aid in producing an integral composite that is useful for making the operative wall of a device. The surfactants act by regulating the surface energy of materials to improve their blending into the composite. The composite material is used for manufacturing devices that maintain their integrity in the environment of use during the agent release period. Generally, the surfactants are amphipathic molecules comprised of a hydrophobic part and a hydrophilic part. The surfactants can be anionic, cationic, nonionic or amphoteric. The anionic surfactants include sulfates, sulfonates, carboxylates, esters, amides, alcohols, ethers, aromatic hydrocarbons, aliphatic hydrocarbons, acylated amino acids and peptides. Metal alkyl phosphates are another class of anionic surfactant. Typically, cationic surfactants are primary, secondary, tertiary or quaternary alkylammonium salts, acylated polyamines, and salts of heterocyclic amines. Nonionic surfactants are typically esters and ethers of polyoxyalkylene glycols, polyhydric alcohols, or phenols. Poloxamers are included as nonionic surfactants. Surfactants are discussed in *Surfactant Systems, Their Chemistry, Pharmacy, and Biology*, D. Attwood and A. T. Florence, Chapman and Hall Pub. Co., 1983, pgs 1-8.

Examples of surfactants include potassium laurate, sodium dodecyl sulfate, hexadecylsulphonic acid, sodium dioctylsulphosuccinate, hexadecyl(cetyl)trimethylammonium bromide, dodecylpyridinium chloride, dodecylamine hydrochloride, bile acids and salts, acacia, tragacanth, sorbitan esters (Spans), polysorbates (Tweens), polyoxyethylene lauryl, cetyl, stearyl, and oleyl ethers (Brij analogs), polyoxyethylene stearates (Myrj analogs), poloxamer and polyoxamine type polyoxyethylene-polyoxypropylene derivatives (Pluronic and Tetronic analogs), polyoxyethylated nonylphenols (Igepal analgos), polyoxyethylate-t-octylphenols (Triton analogs); surface active drug agents such as phenothiazines and tricyclic antidepressants, and the like.

Suitable surfactants can be selected from the above and from other surfactants for blending with wall forming materials by using the surfactant's hydrophile-lipophile balance number, HLB. This number represents the proportion between the weight percentages of hydrophilic and lipophilic groups in a surfactant. In use, the number indicates the behavior of the surfactant, that is, the higher the number the more hydrophilic the surfactant and the lower the number the more lipophilic the surfactant. The required HLB number for blending wall forming materials is determined by selecting a surfactant with a known HLB number, blending it with the materials and observing the results. A uniform composite is formed with the correct HLB number, while a non-uniform mixture indicates a different number is needed. This new number can be selected by using the prior HLB number as a guide. The HLB number is known to the art for many surfactants, and they can be experimentally determined. Generally a HLB number of 10 or less indicates lipophilic behavior and 10 or more indicates hydrophilic behavior. Also, HLB numbers are algebraically additive. Thus, by using a low number with a high number, blends of surfactant can be prepared having numbers intermediate between the two numbers. The concept of HLB is detailed in *Remington's Pharmaceutical Sciences*, 16th Ed., Mack Pub. Co., (1980), pages 316-319. The amount of surfactant needed is an amount that when blended with wall forming materials will form the desired wall composite, and it will vary according to the particular surfactant and materials that are blended to form the wall. Generally, the amount of surfactant will range from about 0.001 part up to 40 parts for 100 parts of wall.

The layer of fluid soluble material which may be positioned between a semipermeable wall containing a hole(s) and a microporous wall, comprises a layer of material selected from organic or inorganic compounds that are soluble in the fluid of the environment of use; drug may optionally be included. Fluid entering the system (commonly water) dissolves the layer to form a solution which is released to the exterior through the microporous wall. Drug laden solution exiting the hole(s) in the semipermeable wall enters this fluid layer at a rate controlled by the semipermeable wall from where the drug is released to the exterior through the microporous wall. Representative inorganic compounds that can be used for forming the layer include magnesium chloride, sodium chloride, lithium chloride, potassium chloride, sodium carbonate, potassium carbonate, manganese carbonate, sodium sulfite, potassium sulfite, lithium sulfite, magnesium sulfate, calcium bicarbonate, sodium bicarbonate, potassium bicarbonate, sodium sulfite, potassium sulfite, lithium sulfite, magnesium sulfite, potassium acid phosphate, sodium acid phosphate, and the like. Typical organic compounds include carbohydrates such as glucose, sucrose, fructose, raffinose and lactose, and other organic compounds soluble in water and biological fluids such as mannitol, sorbitol, polyvinylpyrrolidone, inositol, urea, magnesium succinate, tartaric acid, and the like.

The following examples illustrate the preparation of the drug-delivery devices of this invention and their controlled release of one or more therapeutically active ingredients into an environment of use and as such are not to be considered as limiting the invention set forth in the claims appended hereto.

EXAMPLES

EXAMPLE 1

Figure 3:
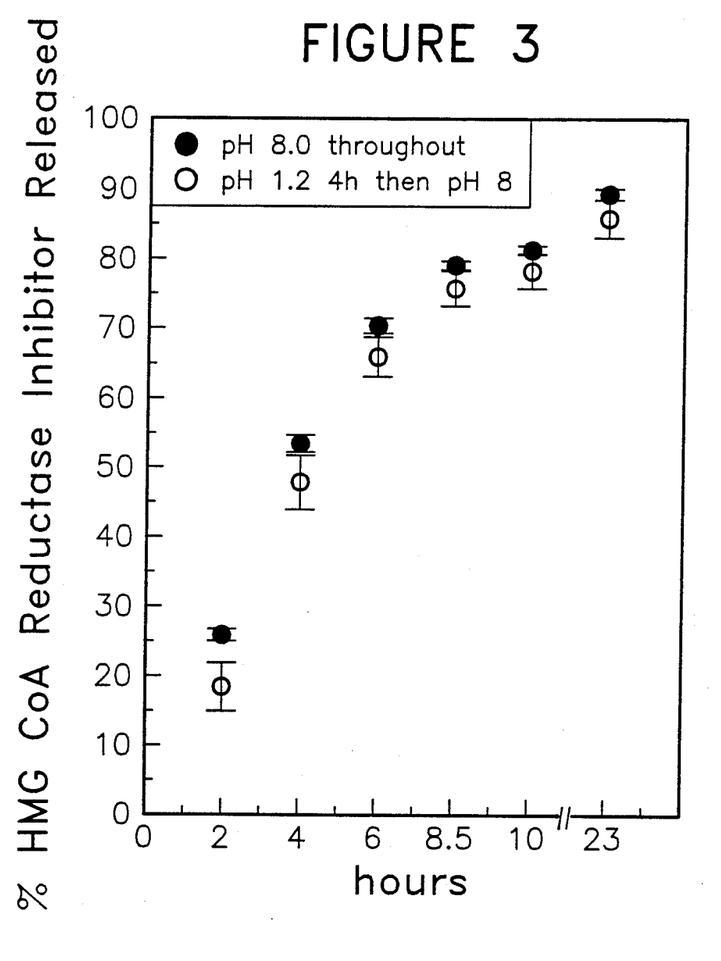
FIGS. 3 and 3a show the average release rates for the devices of Examples 1 and 2, respectively.

A plurality of drug-delivery systems containing the HMG-CoA reductase inhibitor, 7-[1,2,6,7,8,8a(R)hexahydro- 2(S),6(R)-dimethyl-8(S)-(2,2 dimethylbutyryloxy)-naphthalenyl- 1(S)]-3(R),5(R) dihydroxyheptanoate tris(hydroxymethyl)methylammonium salt and Dowex 50X 8-100, a negatively charged resin were prepared. A wet granulation was made containing 7-[1,2,6,7,8,8a(R)-hexahydro-2(S),6(R)-dimethyl- 8(S)-(2,2-dimethylbutyryl-oxy)-naphthalenyl-1(S)]-3(R),5(R)-dihydroxyheptanoate tris(hydroxymethyl)-methylammonium salt:tromethamine free base:mannitol:Dowex 50X 8-100:polyvinyl-pyrrolidone: butylated hydroxyanisole mixed in a 1:4.13:3.94:1.97: 0.98:0.0024 ratio. The dried granules were lubricated with magnesium stearate (0.5% w/w) and compressed into 305 mg core compartments with a ⅜" standard concave tabletting die on a Stokes F-press tabletting machine. Next, a 350 μm thick microporous coat was applied to these cores. 54 g cellulose acetate having an acetyl content of 39% and 18 g cellulose acetate having an acetyl content of 32% were dissolved in a dichloromethane/methanol solvent blend. To this was added 52 g sorbitol and 14.4 g polyethylene glycol 400 dissolved in a water/methanol solvent blend. The composite solution contained water:methanol:dichloromethane in an approximate 1:10:15 ratio. This solution was sprayed onto cores in a Uni-Glatt fluidized bed coating machine. The in vitro release of 7-[1,2,6,7,8,8a(R)-hexahydro-2(S),6(R)-dimethyl-8(S)-(2,2-dimethylbutyryloxy)-naphthalenyl-1(S)]-3(R),5(R)-dihydroxyheptanoate tris(hydroxymethyl)methylammonium salt from these devices into 900 ml volumes of 37° C., pH 1.2 HCl buffer and pH 8.0 phosphate buffer, both made isotonic with sodium chloride, was monitored using a USP Dissolution Method 2 apparatus with constant stirring at 50 rpm. Devices evaluated at pH 1.2 were transferred after 4 hours into the pH 8 media to simulate the variable pH conditions of the human gastrointestinal tract. HPLC was used to assay for drug. The release profiles of 7-[1,2,6,7,8,8a(R)-hexahydro-2(S),6(R)-dimethyl-8(S)-(2,2-dimethylbutyryloxy)-naphthalenyl-1(S)]-3(R),5(R) dihydroxyhept anoate tris(hydroxymethyl)methylammonium salt are shown in FIG. 3. The profiles were prolonged with approximately 70% released at a nearly constant rate.

EXAMPLE 2

Figure 3A:
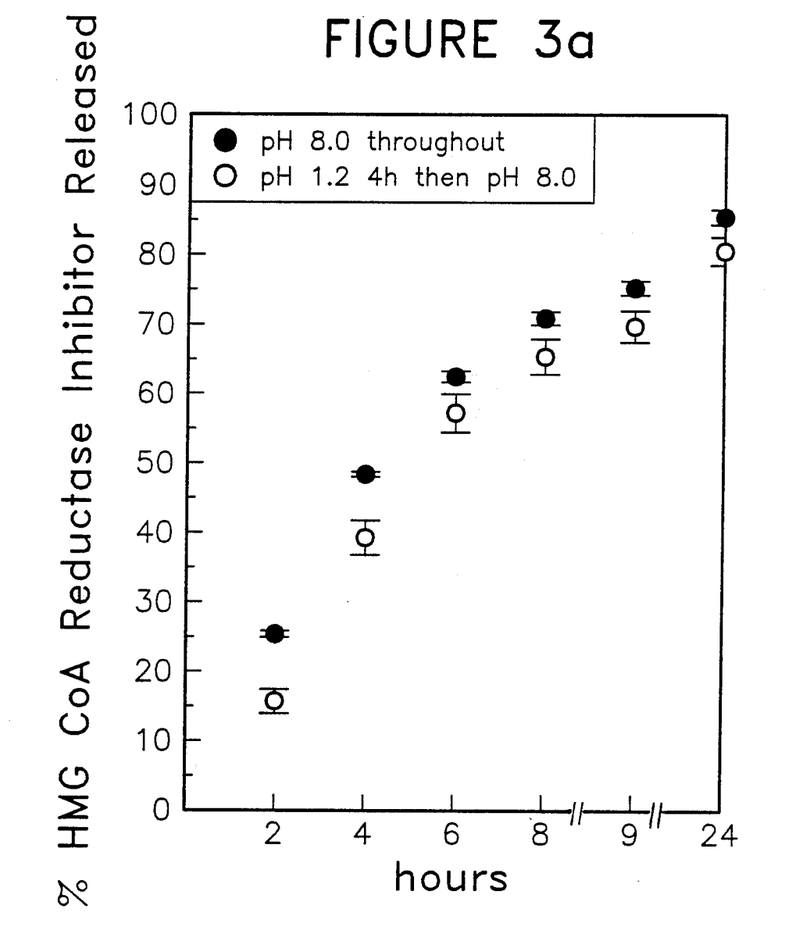

Core tablets were prepared from components as described in Example 1, substituting the anionic resin Amberlite IRP-64 for Dowex 50X 8-100, in a ratio of 1:4.13:3.94:1.77:0.98:0.0024 300 mg cores were compressed in a ⅜" standard concave tabletting die on a Stokes F-press. A microporous coating was applied to the cores by fluidizing bed coating techniques. The coating solution was prepared in a water:methanol:methylene chloride (1:10:15) cosolvent containing 54 g cellulose acetate 398-30, 18 g cellulose acetate 320S, 52 g sorbitol, and 7.2 polythylene glycol 400. A microporous wall approximately 370 μm thick was applied. The release profiles were generated as described in Example 1 and are shown in FIG. 3a.

EXAMPLE 3

A plurality of drug delivery systems containing Amberlite IRP-64 as a negatively charged resin are prepared as follows: a wet granulation is made containing the HMG-CoA reductase inhibitor, 7-[1,2,6,7,8,8a(R)-hexahydro-2(S),6(R)-dimethyl-8(S)-(2,2-dimethylbutyryloxy)-naphthalenyl-1(S)]-3(R),5(R)-dihydroxyheptanoate tris(hydroxymethyl)methylammonium salt, tromethamine, mannitol, Amberlite IRP-64, polyvinyl pyrrolidone, and butylated hydroxyanisole mixed 1:4:4:2:1:0.003, respectively. Core tablets are prepared by compressing 300 mg aliquots of the dried granulation into a ⅜" standard concave tabletting die with a single station Stokes F-press. Next, a semipermeable wall is applied to these cores. 18 g cellulose acetate having an acetyl content of 32% and 54 g cellulose acetate having an acetyl content of 39% are dissolved in a dichloromethane/methanol solvent blend. To this is added 20 g polyethylene glycol 400 as a flux enhancer/plasticizer dissolved in a water/methanol solvent blend. The composite solution contains water:methanol:dichloromethane in an approximate 1:10:15 ratio. This solution is sprayed onto the cores in a commercial Uni-Glatt fluidized bed coating machine. A wall 100 to 200 microns thick is applied. A hole 0.15 mm in diameter is drilled through the semipermeable wall to provide a means of release for the core composition.

EXAMPLE 4

A plurality of drug delivery devices are prepared with the HMG-CoA reductase inhibitor, 7-[1,2,6,7,8,8a(R)-hexahydro-2(S),6(R)-dimethyl-8(S)-(2(S)-methylbutyryloxy)-naphthalenyl-1(S)]-3(R),5(R)-dihydroxyheptanoate tris(hydroxymethyl)methylammonium salt and the negatively charged insoluble resin amberlite IRP-64. A wet granulation is made containing 7-[1,2,6,7,8,8a(R)-hexahydro-2(S),6(R)-dimethyl-8(S)-(2(S)-methylbutyryloxy)-naphthalenyl-1(S)]-3(R),5(R)-dihydroxyheptanoate tris(hydroxymethyl) methylammonium salt, tromethamine, mannitol, Amberlite IRP 64, polyvinylpyrrolidone, and butylated hydroxyanisole mixed 1:4:4:2:1:0.003, respectively. Core compartments are made by compressing 300 mg aliquots of the dried granules into a ⅜" standard concave tabletting die as in Example 1. Next, a microporous wall is applied. 36 g cellulose acetate having an acetyl content of 39% and 36 g cellulose acetate having an acetyl content of 32% are dissolved in an acetone/methanol solvent blend. To this is added 54 g nicotinamide as pore former and 40g polyethylene glycol 400 as a flux enhancer/plasticizer dissolved in methanol. This solution is sprayed onto the cores in a Uni-Glatt fluidized bed coating machine to form a microporous wall 100 microns thick. This microporous wall is then covered by a semipermeable wall as described in Example 3 with a hole 0.15 mm in diameter drilled through both the microporous and semipermeable walls.

EXAMPLE 5

A plurality of core tablets are prepared as described in Example 1. These cores are coated with a semipermeable wall 200microns thick containing a drilled 0.15 mm diameter hole as described in Example 3. The devices are then spray coated with 110 micron thick layer of a water soluble mixture of polyvinylpyrrolidone and sorbitol mixed in a 1:25 weight ratio. This layer is then covered by a microporous wall 110 microns thick by spray coating a dichloromethane/methanol/water solution of a 1:1:1 blend of cellulose acetate having an acetyl content of 32%, celluose acetate having an acetyl content of 39%, and sorbitol. The sorbitol is incorporated as a pore forming additive.

What is claimed is:

1. A drug-delivery device for the controlled release of an HMG-CoA reductase inhibitor salt into an environment of use which comprises:
   (A) a core composition comprising
      (1) a water insoluble, non-diffusible, charged resin entity, and
      (2) a diffusible, water soluble, ionizable HMG-CoA reductase inhibitor salt carrying the same charge as said resin entity; and
   (B) an imperforate water insoluble wall surrounding said core composition and prepared from a semipermeable material substantially impermeable to core composition and permeable to the passage of an external fluid in the environment of use, with said wall having a means for release of the therapeutic agent through the water insoluble wall; or
   (C) a water insoluble wall surrounding said core composition and prepared from (1) a polymer material that is permeable to water but substantially impermeable to solute and (2) 0.1 to 75% by weight, based on the total weight of (1) and (2), of at least one water leachable pore forming additive dispersed throughout said wall.

2. A drug-delivery device according to claim 1 wherein the specific tromethamine salt of HMG-CoA reductase inhibitors is the compound represented by the following structural formula (I):

wherein:
R¹ is selected from:
   (1) $C_{1-10}$ alkyl;
   (2) substituted $C_{1-10}$ alkyl in which one or more substituent(s) is selected from
      (a) hydroxy,
      (b) $C_{1-5}$ alkoxycarbonyl,
      (c) $C_{1-5}$ acyloxy,
      (d) $C_{3-8}$ cycloalkyl, and
      (e) phenyl and;
   (3) $C_{3-8}$ cycloalkyl;
R² is selected from:
   (1) methyl;
   (2) substituted $C_{1-10}$ alkyl in which the substituent is selected from:
      (a) hydroxy, or
      (b) $C_{1-5}$ acyloxy, and
   (3) $C_{1-5}$ alkoxycarbonyl and;
   (4) hydroxy; and
a, b, c and d each represent single bonds or one of a, b, c and d represents a double bond or both a and c or both b and d represent double bonds, provided that when a is a double bond, $R^2$ is methyl, substituted $C_{1-10}$ alkyl or $C_{1-5}$ alkoxycarbonyl.

3. A drug-delivery device according to claim 2 wherein:
$R^2$ is selected from:
(1) methyl; or
(2) hydroxy.

4. A drug delivery device according to claim 3 wherein:
$R^1$ is $C_{1-10}$ alkyl.

5. A drug-delivery device according to claim 4 wherein:
$R^1$ is 1-methylpropyl or 2,2-dimethylpropyl.

6. A drug-delivery device according to claim 5 wherein both a and c represent double bonds.

7. A drug-delivery device according to claim 6 in which the active ingredient is selected from:
(1) 7-[1,2,6,7,8,8a(R)-hexahydro-2(S),6(R)dimethyl-8(S)-(2,2 dimethylbutyryloxy)-naphthalenyl-1(S)]-3(R),5(R)-dihydroxyheptanoate tris(hydroxymethyl)methylammonium salt;
(2) 7-[1,2,6,7,8,8a(R)-hexahydro 2(S),6(R)-dimethyl-8(S)-(2(S)-methylbutyryloxy)-naphthalenyl-1(S)]-3(R),5(R)-dihydroxyheptanoate tris(hydroxymethyl)methylammonium salt;
(3) 7-[1,2,6,7,8,8a(R)-hexahydro-2(S)-methyl 6(R)-hydroxy-8(S)-(2(S)-methylbutyryloxy)-naphthalenyl-1(S)]-3(R),5(R)-dihydroxyheptanoate tris(hydroxymethyl)methylammonium salt; and
(4) 7-[1,2,6,7,8,8a(R)-hexahydro-2(S)-methyl 6(S)-hydroxy-8(S)-(2(S)-methylbutyryloxy)-naphthalenyl-1(S)]-3(R),5(R)-dihydroxyheptanoate tris(hydroxymethyl)methylammonium salt.

8. A drug-delivery device according to claim 1, wherein the resin entity is
(a) an anionic resin with acrylic, methacrylic, polystyrene or phenolic polymeric backbones with phosphonic acid or carboxylic acid active groups;
(b) an anionic resin with polystyrene or phenolic polymeric backbones containing an active group of sulfonic acid;
(c) anionic cellulose polymers selected from the group consisting of sulfoethyl cellulose, sulfopropyl cellulose, and phosphorylated cellulose.

9. A drug-delivery device according to claim 1, wherein the therapeutically active ingredient is soluble in an external fluid and exhibits an osmotic pressure gradient across the wall against the external fluid.

10. A drug-delivery device according to claim 1, wherein the therapeutically active ingredient has limited solubility in the external fluid and is mixed with an osmotically effective solute that is soluble in the fluid, which exhibit an osmotic pressure gradient across the wall against the external fluid.

11. A drug-delivery device according to claim 10, which further comprises in the core a member selected from water soluble excipients, buffers, insoluble buffers, bulking agents, and osmotic regulators.

12. A drug-delivery device according to claim 1, wherein the water insoluble wall surrounding said core composition and prepared from (1) a polymer material that is permeable to water but substantially impermeable to solute and (2) 0.1 to 75% by weight, based on the total weight of (1) and (2), of at least one water leachable pore forming additive dispersed throughout said wall.

13. A drug-delivery device according to claim 12, wherein said pore forming additive comprises:
(a) 0.1 to 50%, by weight, solid additive, based on the total weight of (1) and (2), and/or
(b) 0.1 to 40%, by weight, liquid additive, based on the total weight of (1) and (2), not to exceed a total weight % of pore forming additive of 75%.

14. A drug-delivery device according to claim 13, wherein 0.1 to 50%, by weight, of said pore forming additive is used.

15. A drug-delivery device according to claim 14, wherein said pore forming additive is selected from the group consisting of water, alkali metal salts, alkaline earth metal salts, saccharides, aliphatic polyols, aromatic polyols, nicotinamide, and mixtures thereof.

16. A drug-delivery device according to claim 15, wherein said pore forming additive is selected from the group consisting of polyethylene glycol, sorbitol, glucose and mixtures thereof.

17. A drug-delivery device according to claim 1, wherein the imperforate water insoluble wall surrounding said core composition and prepared from a semipermeable material substantially impermeable to core composition and permeable to the passage of an external fluid in the environment of use, with said wall having a means for release of the therapeutic agent through the water insoluble wall.

* * * * *